(12) United States Patent
Givens et al.

(10) Patent No.: US 11,571,324 B2
(45) Date of Patent: Feb. 7, 2023

(54) OSTOMY POUCH WITH TORTUOUS PATH

(71) Applicant: Hollister Incorporated, Libertyville, IL (US)

(72) Inventors: William Givens, Antioch, IL (US); Adel M. Sadik, Fox River Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 658 days.

(21) Appl. No.: 16/094,340

(22) PCT Filed: May 3, 2017

(86) PCT No.: PCT/US2017/030789
§ 371 (c)(1),
(2) Date: Oct. 17, 2018

(87) PCT Pub. No.: WO2017/192685
PCT Pub. Date: Nov. 9, 2017

(65) Prior Publication Data
US 2021/0228399 A1  Jul. 29, 2021

Related U.S. Application Data

(60) Provisional application No. 62/331,605, filed on May 4, 2016.

(51) Int. Cl.
*A61F 5/44* (2006.01)
(52) U.S. Cl.
CPC .................. *A61F 5/4405* (2013.01)

(58) Field of Classification Search
CPC ......... A61F 5/4405; A61F 5/441; A61F 5/445
See application file for complete search history.

(56) References Cited

U.S. PATENT DOCUMENTS

| 5,401,264 | A | 3/1995 | Leise, Jr. |
| 5,690,623 | A | 11/1997 | Lenz et al. |
| 5,693,035 | A | 12/1997 | Leise, Jr. et al. |
| 6,328,719 | B1 * | 12/2001 | Holtermann ............ A61F 5/441 604/332 |

(Continued)

FOREIGN PATENT DOCUMENTS

| DE | 3237127 A1 | 4/1984 |
| EP | 0116363 A1 | 8/1984 |

(Continued)

OTHER PUBLICATIONS

International Preliminary Report on Patentability issued by International Bureau in connection with PCT/US2017/030789 dated Nov. 15, 2018.

*Primary Examiner* — Tatyana Zalukaeva
*Assistant Examiner* — Hans Kaliher
(74) *Attorney, Agent, or Firm* — Levenfeld Pearlstein, LLC

(57) ABSTRACT

An ostomy pouch includes an outer wall (12) having an inlet opening (24) and a filter (20), the outer wall defining an interior volume (14), an internal wall structure (16) disposed within the interior volume, a one-way valve (22) connected to the internal wall structure, and a path (18) formed by the internal wall structure, the path having an opening (28) at one end and the one-way valve at another end, wherein the filter is positioned within the path.

3 Claims, 2 Drawing Sheets

(56) References Cited

U.S. PATENT DOCUMENTS

| | | | |
|---|---|---|---|
| 6,685,684 B1* | 2/2004 | Falconer | A61F 5/441 604/332 |
| 6,712,800 B2 | 3/2004 | Kanbara | |
| 8,764,716 B2 | 7/2014 | Christensen | |
| 2003/0014023 A1 | 1/2003 | Kanbara | |
| 2008/0306459 A1* | 12/2008 | Albrectsen | A61F 5/441 604/333 |
| 2009/0171306 A1* | 7/2009 | Worsoee | A61F 5/441 29/428 |
| 2010/0016819 A1* | 1/2010 | Gill | A61F 5/4405 604/333 |
| 2011/0196323 A1* | 8/2011 | Gill | A61F 5/445 604/333 |

FOREIGN PATENT DOCUMENTS

| | | | |
|---|---|---|---|
| GB | 2512655 A | 10/2014 | |
| WO | 2007134608 A2 | 11/2007 | |
| WO | 2007134608 A3 | 3/2008 | |
| WO | 2011150936 A1 | 12/2011 | |

* cited by examiner

OSTOMY POUCH WITH TORTUOUS PATH

This is a National Stage Application of International Patent Application No. PCT/US2017/030789, filed May 3, 2017, which claims the benefit of and priority to U.S. Provisional Application No. 62/331,605, filed May 4, 2016, the entirety of which are incorporated fully herein by reference.

BACKGROUND

The following description relates to an ostomy appliance, and in particular, an ostomy bag or pouch having an internal structure forming a path configured to direct liquid and/or solid waste away from a filter.

An ostomy appliance or system is a medical device or prosthetic that provides a means for collecting waste from a stoma typically created as a result of a surgical procedure to divert a portion of the colon or small intestine. One type of ostomy appliance is an ostomy pouch system that may be attached to an ostomate around the stoma or the peristomal area.

An ostomy bag or pouch includes an opening configured to receive the stoma so that liquid or solid bodily waste discharged from the stoma may be collected within the pouch. The pouch also includes a coupling ring to allow the pouch to be secured to the ostomate, for example, by way of a corresponding coupling ring adhered to the patient. Further still, some known pouches include a filter disposed in a wall. The filter is typically located nearly opposite to the opening or coupling ring on the pouch. Thus, when bodily waste, such as stool, is introduced into the pouch, the waste may come into contact with and potentially clog the filter.

Some ostomy bags include features designed to direct bodily waste away from the filter. For example, U.S. Pat. No. 5,690,623 discloses an ostomy pouch having a deodorizing gas filter. The pouch includes an interior barrier wall that divides the interior of the pouch into first and second chambers, and the filter located in the second chamber. The barrier wall operates to block passage of solids and most liquids from the first chamber to the second chamber. A vent is provided in the barrier wall to permit gas flow from the first chamber to the second chamber. A filter protecting panel in the second chamber directs the gas along a circuitous route as the gas travels from the vent to the outlet and filter.

U.S. Pat. No. 6,712,800 discloses an ostomy bag having an inlet at a first side and a gas-discharging vent at a second side. A deodorizing filter is disposed in communication with the gas-discharging vent. An intermediate wall is disposed between the first side and second side, made of a liquid-impermeable material, and divides a space within the bag into two regions. The intermediate wall includes fluid inlets that allow for gases to pass from the region where waste is received in the pouch to the region where the gas-discharging vent and deodorizing filter are positioned.

However, in conventional ostomy pouches, such as those described above, air flow within the pouch and to the filter is restricted by the intermediate barriers. In addition, liquid and/or solid waste contents (i.e., the bodily waste) stored in the pouch may backflow through vents or fluid flow paths formed in an intermediate barrier. As a result, the waste contents may block the vents, and potentially, the filter. Further, the intermediate barriers and other structures may be complex and require additional material, manufacturing steps, labor, costs and assembly time.

Another ostomy bag, as disclosed in U.S. Pat. No. 8,764,716, includes multiple non-return valves configured to prevent or limit back flow of bodily waste within the pouch to the filter. However, such an ostomy bag does not have structure defining a path to direct waste away from a filter. In addition, such an ostomy bag having multiple non-return valves may be complex, time consuming and costly to manufacture.

Accordingly, it is desirable to provide an ostomy bag or pouch configured to direct solid and/or liquid bodily waste away from a filter while allowing sufficient airflow within the bag or pouch to the filter.

SUMMARY

In one embodiment, there is provided an ostomy pouch having an outer wall having an inlet opening and a filter, the outer wall defining an internal volume, an internal wall structure disposed within the internal volume, a one-way valve connected to the internal wall structure and a path defined by the internal wall structure, the path having an opening at one end and the one-way valve at another end, wherein the filter is positioned within the path. The inlet opening may be positioned at one side of the outer wall and the filter may be positioned at an opposite side.

According to another aspect, there is provided an ostomy pouch having a proximal pouch wall and a distal pouch wall connected together along an outer periphery to define an interior volume between the proximal pouch wall and the distal pouch wall, an inlet opening for receiving waste into the pouch, a filter disposed on one of the distal pouch wall and the proximal pouch wall, a first internal wall disposed in the interior volume having a first end spaced from the periphery and a second end, a second internal wall disposed in the interior volume and positioned at least partially between the first internal wall and the filter, the second internal wall having a third end positioned at the periphery and a fourth end spaced from the periphery, and a one-way valve positioned at the second end of the first internal wall. The first internal wall and second internal wall form a path within the interior volume, the path disposed in fluid communication with a collection area of the interior volume. The filter is positioned in the path.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
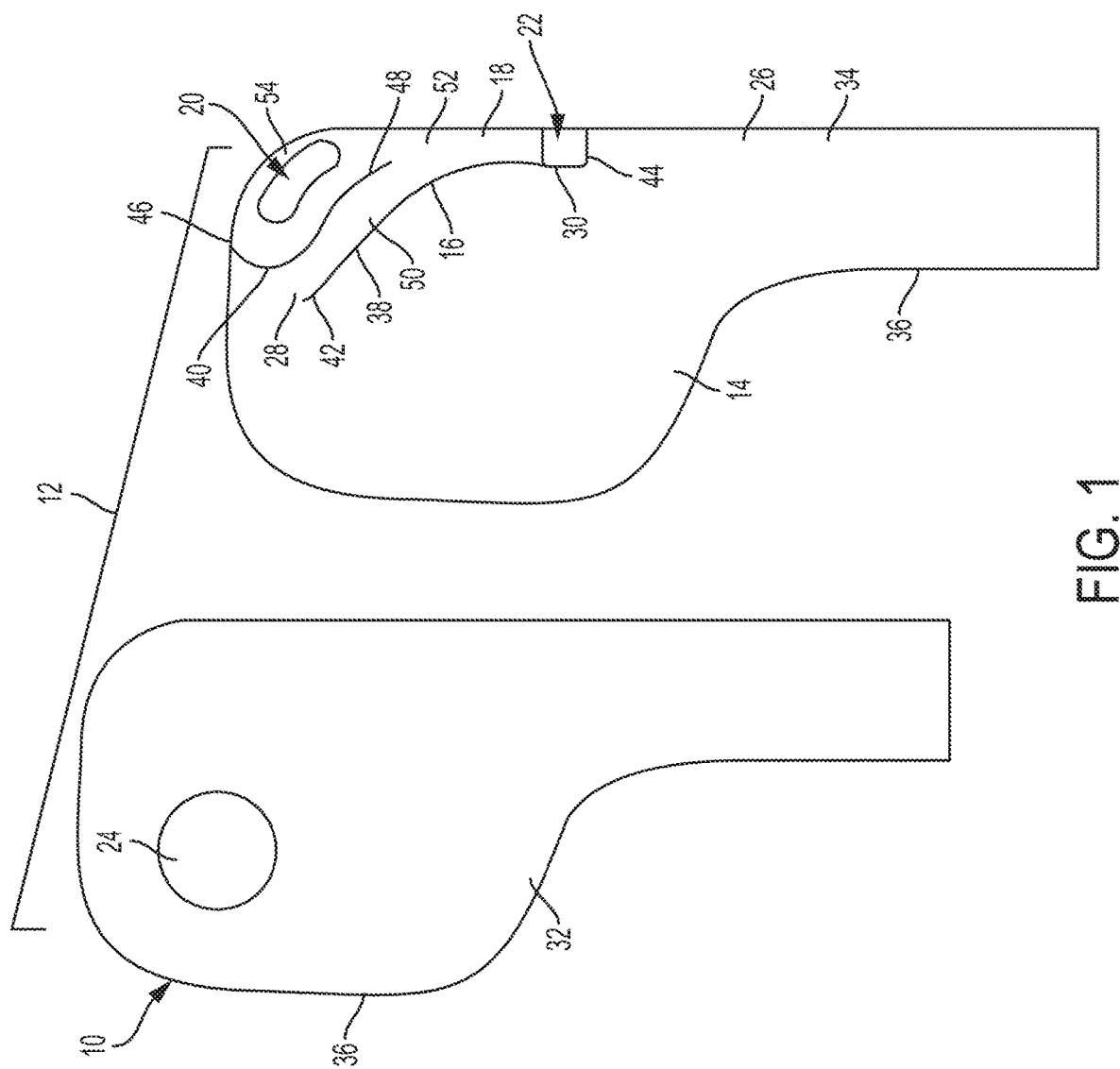
FIG. 1 is an exploded view of an ostomy pouch according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

An ostomy pouch 10 according to the embodiments described herein generally includes an outer wall 12 defining an interior volume 14, the interior volume 14 having an internal wall structure 16 forming a path 18. The outer wall 12 includes a filter 20 positioned in the path 18. Accordingly, bodily waste received in the interior volume 14 may be deflected or diverted away from the filter 20 by the internal wall structure 16, while a gas in the interior volume 14 may flow in the path 18 to the filter 20. Further, a one-way valve 22 is positioned at an end of the path 18 configured to allow egress of liquid or solid waste from the path 18. In one embodiment, the internal wall structure 16 extends between opposite sides of, and is sealed to or formed as one piece with the outer wall 12.

Referring to FIG. 1, in one embodiment, the outer wall 12 includes an inlet opening 24 configured to receive bodily waste from a stoma (not shown). The filter 20 may be positioned substantially opposite from the inlet opening 24, or alternatively, adjacent to the inlet opening 24. The outer wall 12 also includes an outlet opening (not shown). In one embodiment, the inlet opening 24 is positioned generally at an upper portion of the ostomy pouch 10 and the outlet opening is position generally at a lower portion of the ostomy pouch 10.

The interior volume 14 includes a collection area 26 where bodily waste received from the stoma may be collected and stored as contents of the pouch 10. The internal wall structure 16 forms the path 18 within the interior volume 14, and the path 18 is disposed in communication with the collection area 26. To this end, the path 18 includes an ingress opening 28 formed by the internal wall structure 16 and a discharge end 30. The one-way valve 22 is positioned substantially at or near the discharge end 30. Accordingly, the path 18 is fluidically connected to the collection area 26 by way of the ingress opening 28 and is configured to receive gas from the collection area 26 via the ingress opening 28. Additionally, solid or liquid waste received in the path 18 through the ingress opening 28 may be discharged from the path 18 by way of the one-way valve 22 at the discharge end 30.

The outer wall 12 of the ostomy bag 10 may be formed as a single, one-piece construction (i.e., a one-piece ostomy bag) or by multiple portions connected to one another. For example, in one embodiment, the ostomy bag 10 may be formed as a two-piece construction where the outer wall 12 includes a proximal pouch wall 32 and a distal pouch wall 34 connected to one another along a periphery 36. In one embodiment, the proximal pouch wall 32 and distal pouch wall 34 may be heat sealed together along the periphery 36. However, other suitable connections may be used as well, including, for example, adhesives. Further, in one embodiment, the inlet opening 24 may be formed in the proximal pouch wall 32 and the filter 20 may be disposed in the distal pouch wall 34. Alternatively, the inlet opening 24 and filter 20 may both be disposed in the same pouch wall.

Figure 2:
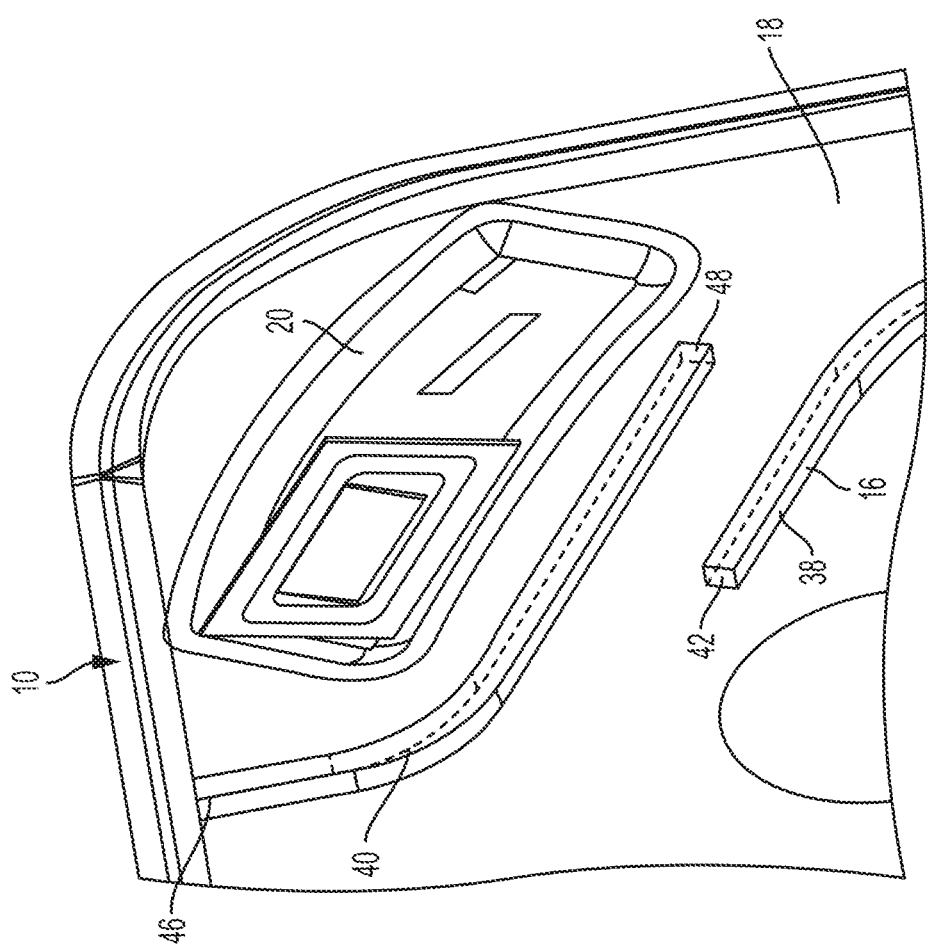
FIG. 2 is an enlarged perspective view of a portion of the ostomy pouch according to an embodiment described herein.

FIG. 2 is an enlarged perspective view of a portion of the ostomy bag 10, including a section of the wall structure 16, according to an embodiment described herein. Referring to FIGS. 1 and 2, in one embodiment, the internal wall structure 16 forms the path 18 as a tortuous path 18 in the interior volume 14. Further, in one embodiment, the internal wall structure 16 includes a first internal wall 38 and a second internal wall 40. The first and second internal walls 38, 40 are spaced from one another along at least portions of their respective lengths such that at least a portion of the path 18 is formed therebetween.

In one embodiment, the first internal wall 38 has a first end 42 spaced from a periphery of the outer wall 12, i.e., at a position within the interior volume 14. The first end 42 corresponds to the ingress opening 28 of the path 18. The first internal wall 38 also has a second end 44 positioned at or near the one-way valve 22, which corresponds to the discharge end 30 of the path 18. The first internal wall 38 may include one or more curves, bends, angles, arcs and the like between the first end 42 and the second end 44.

In one embodiment, the second internal wall 40 includes a third end 46 disposed substantially at the periphery 36, i.e., at a region where oppositely facing walls of the outer wall 12 meet or where the proximal pouch wall 32 and distal pouch wall 34 are joined. The second internal wall 40 also includes a fourth end 48 spaced from the periphery 36 and the discharge end 30 of the path 18. In one embodiment, the second internal wall 40 extends between the first internal wall 38 and the filter 20. A portion the second internal wall 40 may bound a portion of the ingress opening 28 of the path 18. The second internal wall 40 may also include one or more curves, bends, angles, arcs and the like.

The internal wall structure 16 may form the path 18 to have multiple sections. For example, in one embodiment, the path 18 may have first, second and third sections 50, 52, 54. The first section 50 may be fluidically connected to the third section 54 via the second section 52. In one embodiment, the first section 50 may be formed between the first internal wall 38 and the second internal wall 40 and includes the ingress opening 28 at one end. The second section 52 may be formed between the first internal wall 38 and a portion of the outer wall 12 and/or periphery 36. The second section 52 includes the one-way valve 22 at one end. The third section 54 may be formed between the second internal wall 40 and a portion of the outer wall 12 and/or periphery 36. The filter 20 may be disposed in the third section 54. In one embodiment, the second internal wall 40 separates the first section 50 from the third section 54.

In one embodiment, the ostomy pouch 10 described herein may be formed, for example, through injection molding, extruding, or the like. In addition, the internal wall structure 16 may be made, for example, by pressing and heat sealing the desired internal wall geometries between the opposing sides of the outer wall 12, i.e., between the oppositely facing sides of a one-piece pouch construction or the proximal pouch wall 32 and distal pouch wall 34. Thus, the internal wall structure 16, which may include first and second internal walls 38, 40, may be formed integrally as one piece with the outer wall 12. In one embodiment, the internal wall structure 16 may be formed integrally, continuously and as one-piece with at least one of the proximal pouch wall 32 and distal pouch wall 34.

Accordingly, in the embodiments above, bodily waste may be received into the interior volume 14 of the ostomy pouch 10. The internal wall structure 16 is configured to prevent the bodily waste or contents received into the interior space from contacting and clogging the filter 20 by directing the bodily waste into the collection area 26. Gas received in the collection area 26 may move through the ingress opening 28, into the path 18, and to the filter 20 where it may be odor filtered and exit from the ostomy pouch 10. In addition, in the event bodily waste or contents are received into the path 18, the bodily waste or contents may be discharged from the one-way valve at the discharge end 30 of the path. Thus, the bodily waste or contents may be discharged from the path upstream from the filter 20. The one-way valve 22, operating as an anti-reflux valve 22 substantially prevents bodily waste or contents from entering the path 18 at the discharge end 30. Further still, according to the embodiments above, the internal wall structure 16 may be formed from the outer wall 12 by pressing and heat sealing. Thus, additional material is not necessary and manufacturing steps may be reduced compared to constructions where an internal wall is separately added.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy pouch comprising:
   (a) a waste collection pouch comprising: (i) a proximal pouch wall; and (ii) a distal pouch wall connected together along (iii) an outer periphery to define: (iii) an interior volume between the proximal pouch wall and the distal pouch wall; (iv) an inlet opening in the proximal pouch wall for receiving waste into the pouch; and (v) a gas outlet opening in an upper portion of the distal pouch wall or an upper portion of the proximal pouch wall;
   (b) a gas filter adjacent said gas outlet opening, configured to release gas from the internal volume, and attached to the distal pouch wall or the proximal pouch wall covering the gas outlet opening;
   (c) a first heat seal partially enclosing the gas filter and gas outlet opening from the inlet opening; connecting the proximal and distal pouch walls; and having:
      (i) a first end at an upper end of the outer periphery;
      (ii) a second end at a first point below the gas filter and adjacent to, but spaced from, the outer periphery; the first heat seal forming a first gas flow path between the gas filter and a second gas flow path formed by:
   (d) a second heat seal proximate the first heat seal; connecting the proximal and distal pouch walls; and having:
      (i) a third end at a second point between the first heat seal and the inlet opening; and
      (ii) a fourth end below the second end and adjacent to, but spaced from, the outer periphery; the fourth end and the outer periphery forming a valve opening;
   (e) a one-way valve positioned within the valve opening and configured to allow egress of liquid or solid waste from the second flow path and to prevent solid or liquid waste from entering the second flow path from the interior volume.

2. The ostomy pouch of claim 1, wherein the path is tortuous.

3. The ostomy pouch of claim 1, wherein the path includes an ingress opening between the first internal wall and the second internal wall such that the path is fluidically connected to the collection area.

* * * * *